(12) United States Patent
Appling et al.

(10) Patent No.: US 7,396,358 B2
(45) Date of Patent: Jul. 8, 2008

(54) DEVICE AND METHOD FOR CONVERTING A BALLOON CATHETER INTO A CUTTING BALLOON CATHETER

(75) Inventors: William M. Appling, Granville, NY (US); Israel Schur, Englewood, NJ (US); Giorgio di Palma, Queensbury, NY (US)

(73) Assignee: AngioDynamics, Inc., Queensbury, NY (US)

( * ) Notice: Subject to any disclaimer, the term of this patent is extended or adjusted under 35 U.S.C. 154(b) by 59 days.

(21) Appl. No.: 11/293,543

(22) Filed: Dec. 2, 2005

(65) Prior Publication Data

US 2006/0085026 A1 Apr. 20, 2006

Related U.S. Application Data

(62) Division of application No. 10/640,716, filed on Aug. 13, 2003, now Pat. No. 7,131,981.

(60) Provisional application No. 60/457,458, filed on Mar. 25, 2003.

(51) Int. Cl.
*A61B 17/22* (2006.01)
(52) U.S. Cl. ...................................... 606/159
(58) Field of Classification Search .............. 606/200, 606/127, 198, 190, 159, 170
See application file for complete search history.

(56) References Cited

U.S. PATENT DOCUMENTS

| | | | |
|---|---|---|---|
| 3,837,345 A | 9/1974 | Matar | |
| 4,273,128 A | 6/1981 | Lary | |
| 4,765,332 A | 8/1988 | Fischell et al. | |
| 5,009,659 A | 4/1991 | Hamlin et al. | |
| 5,069,679 A | 12/1991 | Taheri | |
| 5,196,024 A | 3/1993 | Barath | |
| 5,282,813 A | 2/1994 | Redha | |
| 5,320,634 A | 6/1994 | Vigil et al. | |
| 5,354,279 A | 10/1994 | Hofling | |
| 5,522,825 A | 6/1996 | Kropf et al. | |
| 5,616,149 A | 4/1997 | Barath | |
| 5,649,953 A | 7/1997 | Lefebvre | |
| 5,725,543 A | 3/1998 | Redha | |
| 5,797,935 A | 8/1998 | Barath | |
| 5,902,213 A | 5/1999 | Tsutsui et al. | |
| 5,941,869 A * | 8/1999 | Patterson et al. | ............ 604/508 |
| 5,947,985 A * | 9/1999 | Imran | ......................... 606/159 |
| 5,972,019 A * | 10/1999 | Engelson et al. | ............ 606/200 |

(Continued)

FOREIGN PATENT DOCUMENTS

EP 0533321 3/1993

(Continued)

*Primary Examiner*—Todd E. Manahan
*Assistant Examiner*—Elizabeth Houston
(74) *Attorney, Agent, or Firm*—Cowan, Liebowitz & Latman

(57) ABSTRACT

A lesion treating device for converting a standard balloon catheter into a cutting balloon catheter is provided. The device includes a longitudinal housing such as a tube which is sized to be inserted into a lumen of the balloon catheter and cutting wires disposed within the longitudinal housing in an undeployed position. When the longitudinal housing is moved relative to the cutting wires, the cutting wires extend out of the longitudinal housing. The balloon of the balloon catheter is then moved under the deployed cutting wires and inflated to convert the standard balloon catheter into the cutting balloon catheter.

11 Claims, 9 Drawing Sheets

U.S. PATENT DOCUMENTS

| | | | |
|---|---|---|---|
| 6,009,877 A | 1/2000 | Edwards | |
| 6,165,187 A | 12/2000 | Reger | |
| 6,290,710 B1 * | 9/2001 | Cryer et al. | 606/200 |
| 6,315,708 B1 * | 11/2001 | Salmon et al. | 600/3 |
| 6,423,032 B2 | 7/2002 | Parodi | |
| 6,425,909 B1 * | 7/2002 | Dieck et al. | 606/200 |
| 6,485,500 B1 * | 11/2002 | Kokish et al. | 606/194 |
| 6,485,501 B1 * | 11/2002 | Green | 606/200 |
| 6,547,803 B2 | 4/2003 | Seward | |
| 6,620,148 B1 * | 9/2003 | Tsugita | 604/509 |
| 6,620,182 B1 * | 9/2003 | Khosravi et al. | 606/200 |
| 6,663,651 B2 * | 12/2003 | Krolik et al. | 606/200 |
| 6,709,444 B1 | 3/2004 | Makower | |
| 6,746,463 B1 * | 6/2004 | Schwartz | 606/159 |
| 6,755,846 B1 * | 6/2004 | Yadav | 606/200 |
| 6,808,531 B2 | 10/2004 | Lafontaine | |
| 6,964,670 B1 * | 11/2005 | Shah et al. | 606/200 |
| 2002/0029052 A1 | 3/2002 | Evans | |
| 2002/0156520 A1 * | 10/2002 | Boylan et al. | 623/1.11 |
| 2003/0040770 A1 | 2/2003 | Radische, Jr. | |
| 2003/0176886 A1 * | 9/2003 | Wholey et al. | 606/200 |
| 2004/0006306 A1 * | 1/2004 | Evans et al. | 604/101.03 |
| 2004/0006365 A1 * | 1/2004 | Brady et al. | 606/200 |
| 2005/0021071 A1 | 1/2005 | Konstantino, et al. | |
| 2005/0027247 A1 * | 2/2005 | Carrison et al. | 604/101.01 |

FOREIGN PATENT DOCUMENTS

| | | | |
|---|---|---|---|
| JP | 6178781 | | 6/1994 |
| WO | WO 98/33443 | * | 8/1998 |

* cited by examiner

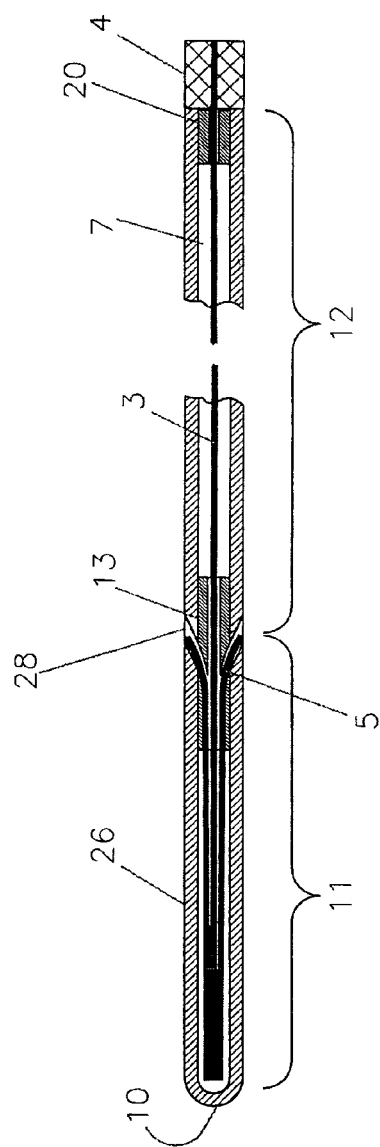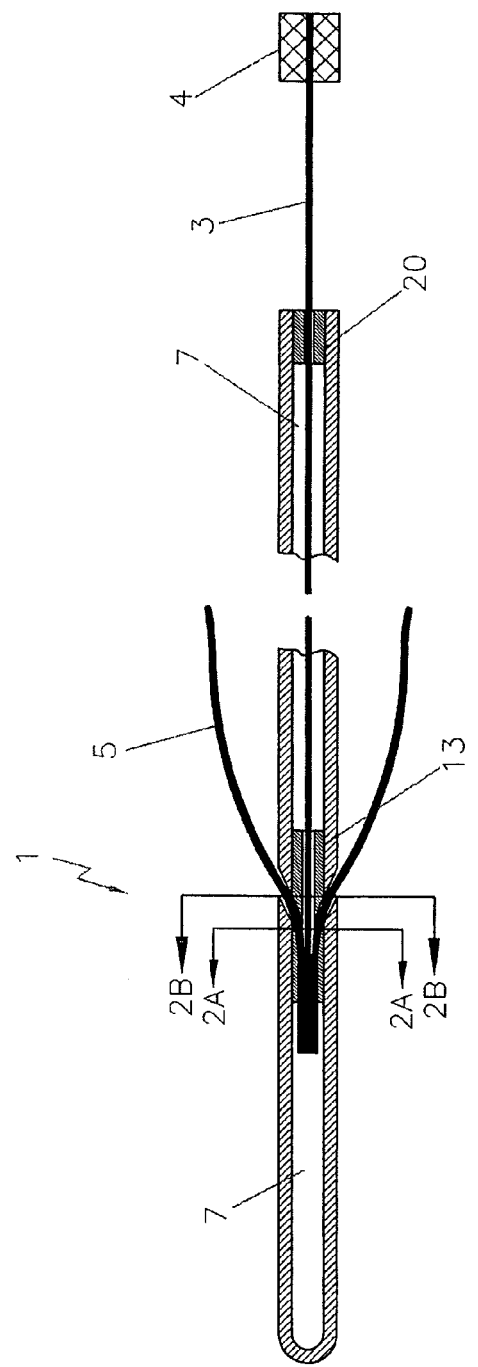
FIG. 1A
FIG. 1B

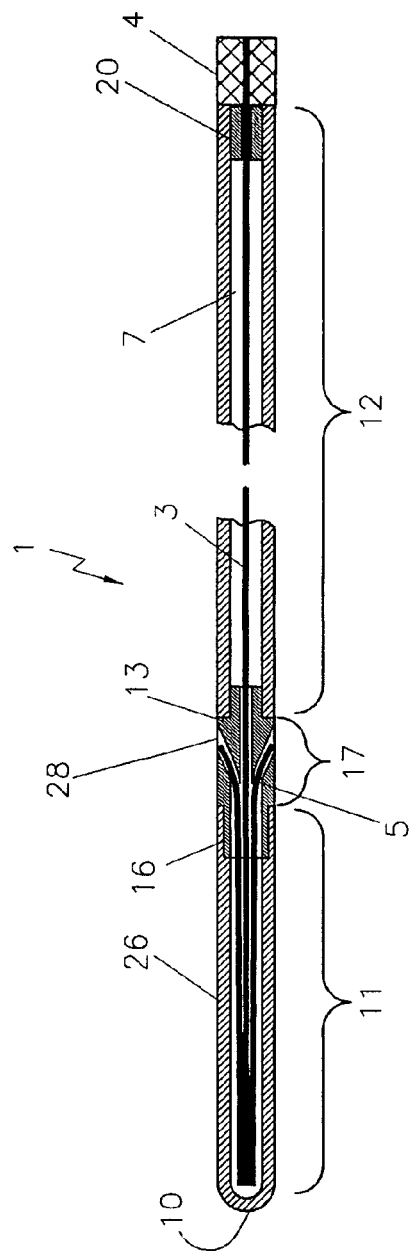
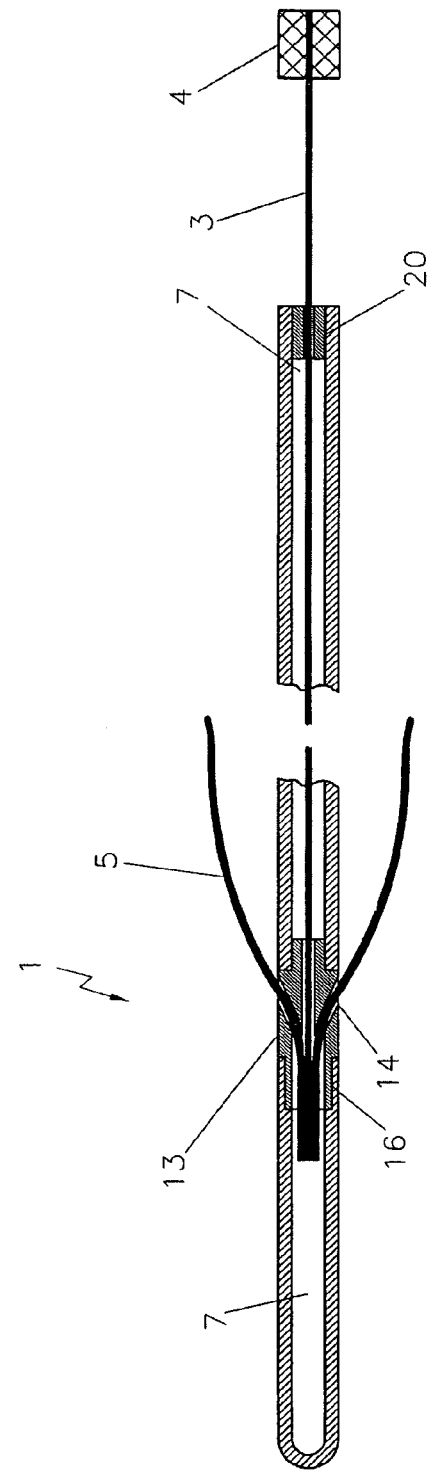
FIG. 3A
FIG. 3B

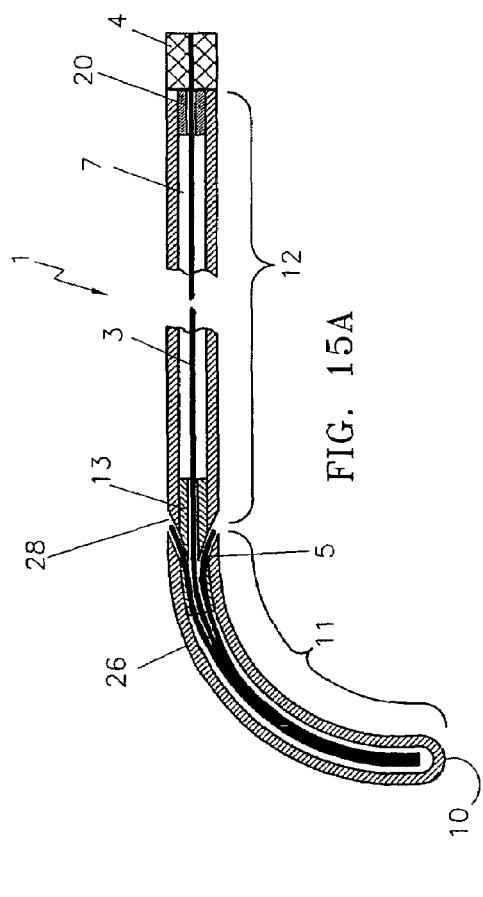
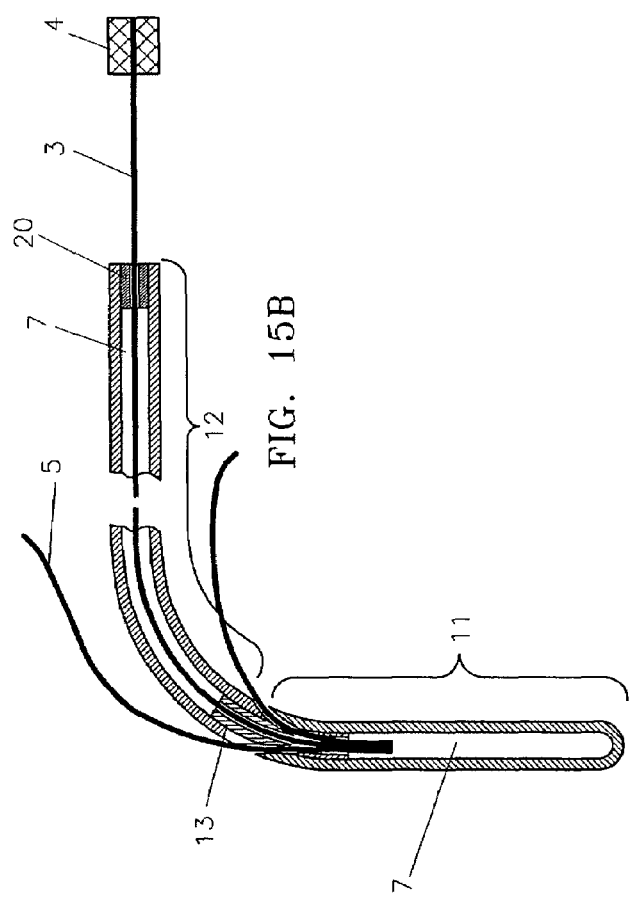

DEVICE AND METHOD FOR CONVERTING A BALLOON CATHETER INTO A CUTTING BALLOON CATHETER

CROSS-REFERENCE TO RELATED APPLICATIONS

This is a division of U.S. application Ser. No. 10/640,716, filed Aug. 13, 2003, now U.S. Pat. No. 7,131,981 which claims priority to provisional application No. 60/457,458, filed Mar. 25, 2003, all of which are incorporated herein by reference.

FIELD OF THE INVENTION

The present invention relates to an intraluminal device, and more particularly to a device for converting a balloon catheter into a cutting balloon catheter.

BACKGROUND OF THE INVENTION

Treatment of stenosis by angioplasty balloon catheters is well known. Typically a lesion can be opened by a standard balloon catheter quickly and easily at moderate inflation pressures. Some stenotic lesions can be highly resistant to opening at reasonable pressures and occasionally balloon catheters are not strong enough to sufficiently open such lesions. For example, when treating a stenosis that occurs at the venous anastomosis of a dialysis graft, it is found that often these lesions require pressure in excess of 28 atmospheres. Such a high pressure increases the degree of vascular trauma caused by the rapid stretching and tearing of the media and adventia layers of the vessel. Vascular trauma to the vessel wall has been shown to increase the ingrowth of smooth muscle cells, which is directly related to increased restenosis rates.

Despite the above drawbacks, high-pressure angioplasty balloons were developed to treat these highly resistant lesions. Typically these catheters require larger sheath sizes than low-pressure balloon catheters and are expensive due to the materials and design required to achieve high pressures.

To address the problems associated with conventional high pressure angioplasty balloons, techniques were developed in which an angioplasty balloon was placed along side of a guidewire and then inflated, creating focal pressure against the lesion along the guidewire surface. This technique became known as the Buddy Wire technique. Scientific studies have demonstrated that the application of slow, low pressure delivered in a focused manner reduces the degree of vessel trauma and thus post-procedure complications including restenosis. Although the technique is still practiced today, there are several disadvantages with the procedure. The technique typically is done with a single "Buddy Wire", resulting in a single focal pressure line against the lesion. The use of more than one wire will address this problem but it is difficult to control the positioning within the lesion of more than one guidewire. Lack of control over guidewire location relative to the balloon makes the procedure more unpredictable and difficult than conventional angioplasty procedures.

In the early 1990s, cutting balloon catheters were developed. Barath disclosed a cutting balloon in U.S. Pat. No. 5,196,024 entitled "Balloon Catheter with Cutting Edge", issued Mar. 23, 1993, which is incorporated herein by reference. Barath's design and other cutting angioplasty balloons have microsurgical cutting wires in the form of blades that are pre-mounted to the surface of the balloon. When the balloon is inflated the blades cut partially through the vessel wall resulting in controlled, localized dissection of the inner vessel layers. The blades produce high focal stress lines along the lesion surface in a controlled, predictable manner. Because the pressure is concentrated along the blades, less balloon inflation pressure is required a to open the stenosis. For example, a lesion that may require 30 atms with standard high pressure angioplasty may open at approximately 8 atms with a cutting balloon device.

Although cutting balloon technology addresses some of the problems associated with conventional angioplasty, there are several drawbacks with the use of cutting balloons. The cutting blades or wires increase the overall profile of the angioplasty device. Specifically, a cutting balloon profile is larger than a conventional Percutaneous Transluminal Coronary Angioplasty (PTCA) or Percutaneous Transluminal Angioplasty (PTA) catheter with the same nominal inflated diameter. Thus, the catheter requires a larger insertion sheath than a standard angioplasty balloon. Difficulties in advancing the balloon through the vasculature to the target lesion are more frequent with a cutting balloon than with a conventional angioplasty balloon of an equivalent inflation diameter due to the larger profile.

Insertion, advancement and placement of cutting balloons are also more difficult because the relatively stiff blade materials prevent the cutting balloon from being as flexible as standard angioplasty catheters. Accordingly, tracking the device through tortuous vasculature is more problematic with the cutting balloon. To increase the flexibility, one conventional catheter incorporated keyhole cutouts in the blades. While the keyhole design increases the overall flexibility of the cutting balloon, it adds complexity to the micro-precision manufacturing process and costs. Radisch attempts to address the blade stiffness problem in his U.S. Patent Application No. 2003/0040770 entitled "Segmented Balloon Catheter Blade", which is incorporated herein by reference. Radisch's design utilizes individual blade segments attached to a base in such a manner as to allow relative movement between adjacent blade segment, thereby providing increased flexibility. Again, while increasing flexibility, the design adds complexity to the manufacturing cost and still does not address the problems associated with increased overall device diameter.

Prior art cutting balloons are also disadvantageous during withdrawal of the device. Some cutting balloon designs use the balloon creases to cover and protect the vessel wall from unintentional incising during withdrawal. One such design is disclosed in U.S. Pat. No. 5,320,634 entitled "Balloon Catheter with Seated Cutting Edges", issued Jun. 14, 1994 to Vigil, which is incorporated herein by reference. While Vigil provides an increased level of protection during withdrawal, there are still disadvantages with the Vigil design. The balloon deflation process is not always controllable and the deflated balloon surface does not always adequately cover the blades. Furthermore, deflation failures, common with angioplasty balloons, may result in significant patient complications when the cutting balloon fails to completely deflate. Unintentional vessel dissection may occur during withdrawal. Balloon rupture and other mechanical failure may result in the necessity of surgically retrieving blade components from the vessel.

Another disadvantage of cutting balloons is cost. The cutting balloons cost approximately four times the cost of a standard balloon catheter. Consequently the cutting balloon catheter is only used when standard angioplasty balloons fail to open a lesion. Even so, the medical facility needs to carry a complete inventory of both standard and cutting balloons in order to be prepared to treat various size lesions. This becomes very expensive and requires a large inventory space.

Barath attempts to overcome this problem in U.S. Pat. No. 5,797,935 entitled "Balloon Activated Forced Concentrators for Incising Stenotic Segments", issued Aug. 25, 1998, which is incorporated herein by reference. He discloses the use of a separate "activated force concentrator" component that is mounted over a standard angioplasty balloon prior to insertion.

Although Barath's device allows customization of a standard angioplasty balloon for a variety of procedures and thus reduces inventory requirements, it does have several deficiencies. The concentrator is user-mounted on the balloon prior to insertion into the patient. The concentrator increases the overall profile of the device resulting in insertion and advancement complications as previously discussed. Even after deflation in its reduced profile, the atherotomes or blades remain exposed and may thus increase the possibility of unintentional incision of non-target vessel segments during withdrawal. Another disadvantage of Barath's concentrator design relates to balloon inventory-stocking levels. Although Barath's design reduces the inventory requirements for angioplasty procedures, each balloon length would require a separate concentrator length thus introducing complexity and additional inventory parts into the angiosuite. In addition, the difference in balloon specifications among manufacturers makes custom fitting of the concentrator to the balloon difficult.

Still another disadvantage of cutting balloons is that a physician is required to remove the standard angioplasty catheter already in the vessel and insert in its place the cutting balloon catheter. In general, cutting balloons are intended for use only after conventional angioplasty has failed to successfully restore vessel lumen patency. When that happens, the conventional angioplasty balloon is removed and then the cutting balloon is inserted and advanced to the lesion. With Barath's design, the angioplasty balloon is removed, the concentrator is mounted on the balloon, and then the concentrator-mounted balloon is re-inserted into the vessel. With either approach, the balloon exchanges carry added risk, add time to the procedure, and increase treatment costs due to additional device use.

In addition to replacing the standard catheter with a cutting balloon catheter, often it may be necessary to also replace the guidewire as well. This is because a standard angioplasty balloon may require a 0.035" guidewire, while a cutting balloon catheter may require a smaller diameter 0.018" or 0.014" guidewire. As persons of ordinary skill in the art can appreciate, this procedure carries substantial added risk to the patient, not to mention the increased cost and added procedure time.

Therefore, it is desirable to provide a device and method, which can be used to convert a conventional angioplasty balloon catheter into a cutting balloon catheter without increasing the balloon diameter and without requiring an exchange or re-insertion of the catheter.

It is also desirable to provide such a device and method in which a single unit can accommodate multiple conventional angioplasty balloons of varying diameters and lengths.

It is also desirable to provide such a device and method, which provides protection of the vessel wall from the cutting elements during insertion and withdrawal of the device.

It is also desirable to provide a reliable, inexpensive, efficient and fast method of opening a stenotic lesion that fails to open using conventional angioplasty by converting an already in place angioplasty balloon to a cutting instrument.

It is also desirable to provide such a device and method which substantially reduces the requirement of carrying a complete inventory of both standard and cutting balloons in order to be prepared to treat various size lesions.

SUMMARY OF THE DISCLOSURE

According to the principles of the present invention, a device for treating a lesion in a body lumen is provided. In one embodiment, the device includes a longitudinal housing such as a tube which is operable to be inserted into a lumen of an intraluminal device having an expandable member such as a balloon catheter. At least one wire is coupled to the longitudinal housing in an undeployed position. When the wire is deployed, it extends out from the longitudinal housing such that the balloon of the balloon catheter can be positioned under the deployed wire. When the balloon is inflated, the balloon catheter is converted into a cutting balloon catheter.

In one aspect, the longitudinal housing includes an opening in its sidewall and when the housing is longitudinally moved with respect to the wire, one end of the wire extends through the opening into the deployed position.

In another aspect, the device includes a shaft positioned inside the longitudinal housing and its distal end is attached to the other end of the wire. In this embodiment, the wire is deployed by moving the longitudinal housing in a longitudinal direction with respect to the shaft. If the housing is pushed distally forward while the shaft is held stationary, the one end of the wire extends through the opening into the deployed position without the wire moving longitudinally.

In another aspect, the device includes a guide positioned within the longitudinal housing. The guide has a guide channel which is in communication with the opening in the housing side wall. The guide channel guides the wire when the wire is being extended out of the opening.

In another aspect, the wire includes a longitudinal blade having a cutting edge that points toward a body lumen wall when the wire is extended into the deployed position.

In yet another aspect, when the longitudinal housing is proximally moved with respect to the wire, the wire is retracted through the opening into the undeployed position.

In another aspect of the invention, the device includes multiple cutting wires and multiples openings in the longitudinal housing sidewall with each opening associated with a corresponding cutting wire. First ends of all cutting wires are attached to a shaft while second ends of the cutting wires are located within the channels of the guide and positioned for deployment. To deploy the device, the wires are extended out from the longitudinal housing. Specifically, when the longitudinal housing is longitudinally and distally moved while the shaft is held stationary, the second ends of the cutting wires extend through the respective openings in an umbrella-like configuration to allow the balloon to be positioned under the extended wires.

In another aspect of the invention, a distal portion of the present device has a predetermined curve profile to better accommodate certain curved vessels.

In yet another aspect of the invention, the wire is round and has no cutting edge.

Because the present device is deployed while the standard balloon catheter is still positioned in the vessel, all of the complications and problems associated with exchanging the catheter with a cutting balloon catheter are eliminated. Also, because the present device is inserted through the lumen of a standard balloon catheter, all problems associated with the larger diameter and profile of the conventional cutting balloon catheter, including the difficulty of inserting and advancing the larger catheter, are eliminated.

Another advantage of the present device in certain embodiments is that the length of the deployed wires is designed to be controlled by the amount of their longitudinal movement with respect to the housing. Consequently, a single device can be used with various size balloon catheters. Moreover, because the present device is designed to replace the cutting balloon catheters, this results in a great reduction and even elimination of an entire inventory of the cutting balloon catheters that were previously necessary to treat various size lesions.

Yet another advantage of the present device is that because it is designed to be inserted through a lumen of the balloon catheter, the balloon catheter itself protects the vessel wall from the cutting edges of the wires during insertion and withdrawal of the device unlike the cutting balloon catheters in which the cutting wires may accidentally cut the vessel wall during insertion and withdrawal.

BRIEF DESCRIPTION OF THE DRAWINGS

FIG. 1A is a sectional view of a device of the present invention in an undeployed state.

FIG. 1B is a sectional view of the present device in a deployed state.

FIG. 3A is a sectional view of an alternative embodiment of the present device in an undeployed state.

FIG. 3B is a sectional view of an alternative embodiment of the present device in a deployed state.

FIG. 15A is a sectional view of an alternative embodiment of the present device in an undeployed state.

FIG. 15B is a sectional view of an alternative embodiment of the present device in a deployed state.

DETAILED DESCRIPTION OF THE INVENTION

Figure 2A:
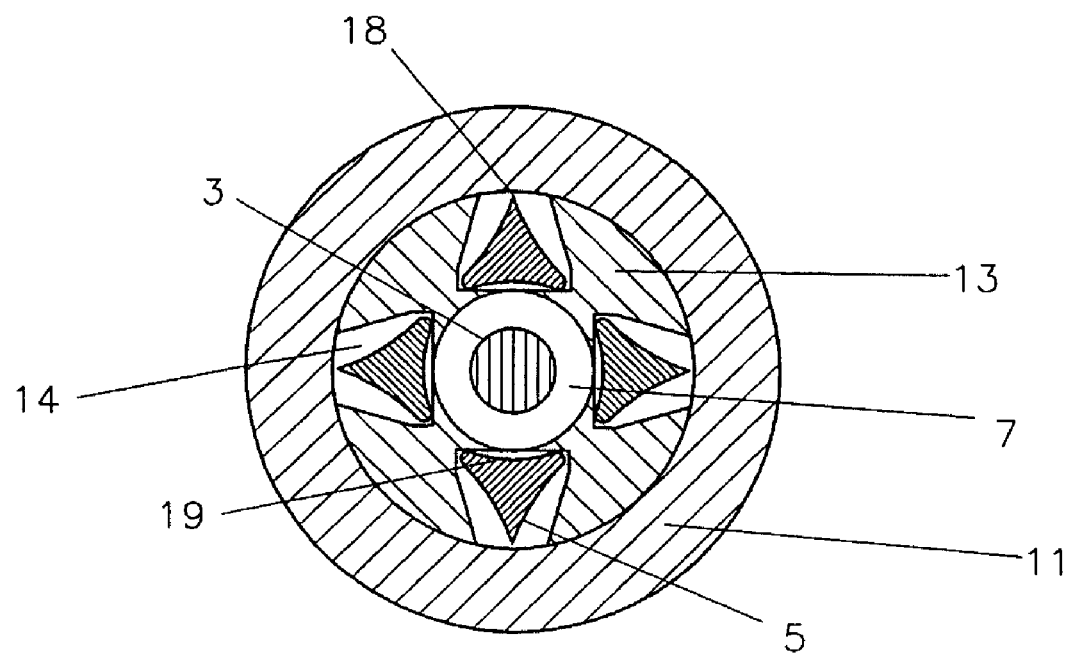
FIG. 2A is a cross-sectional view of the present device as seen along line 2A-2A in FIG. 1B.

Referring to FIG. 1A, a conversion device 1 of the present invention is shown from a sectional view. Longitudinal housing 26 is preferably made from polyimide shaft tubing or other flexible material with sufficient pusbability to navigate tortuous vessel channels. The outer diameter of the tube 26 is dimensioned so as to allow insertion of the device 1 within the guidewire lumen of a standard angioplasty catheter 24 (see FIG. 8). Typically, coronary balloon catheters accept 0.014"-0.018" diameter guidewires. Balloon catheters for peripheral vascular applications accept 0.035" diameter guidewires. Because the conversion device 1 is delivered through the lumen of a standard angioplasty catheter, the problem with large profiles of prior art cutting balloons and the difficulty in insertion and advancement caused by the larger devices is completely eliminated.

The longitudinal housing such as a tube 26 is a continuous tube, defined by two tubular jacket segments with at least one channel or opening 28 through the sidewall of longitudinal housing 26. A guide insert device 13 is disposed within the lumen of the tube 26. A longitudinal channel 7 in the proximal tubular jacket segment 12 is capable of receiving a shaft 3 in the form of a mandrel in the embodiment shown. Channel 7 is terminated at the proximal end by a bushing 20. As illustrated in FIG. 1A and FIG. 1B, the channel 7 of the guide insert 13 has a smaller diameter than the channel 7 of the proximal and distal tubular jacket segments 12 and 111 respectively. Channel 7 terminates at the distal tip 10 of tubular jacket segment 11.

As depicted in FIG. 1A-1B, the guide insert 13 includes the channel 7 having a reduced diameter and four guide channels 14 (FIG. 2A). The reduced channel 7 ensures that the shaft 3 remains longitudinally centered within the channel and provides an alignment function for the cutting wires 5 within guide channels 14. Also, shaft 3 is supported within the channel 7 at the proximal end by bushing 20.

FIG. 2A is a cross-sectional view of the device 1 of FIG. 1B shown along lines 2A-2A. Referring to FIG. 2A, the guide channels 14 form longitudinal grooves within the guide insert 13 through which the cutting wires 5 pass during deployment and retraction into and out of the vessel lumen. The guide channels 14 begin in guide insert 13 and, together with the inner wall of distal tubular segment 11, form a secured and enclosed area for the cutting wire elements 5 during insertion and withdrawal of the device 1. The guide channels 14 facilitate symmetrical deployment of the wires 5. The channels 14 also provide for smooth advancement and retraction of the wire 5 once positioned within the target lesion area of the vessel.

Figure 2B:
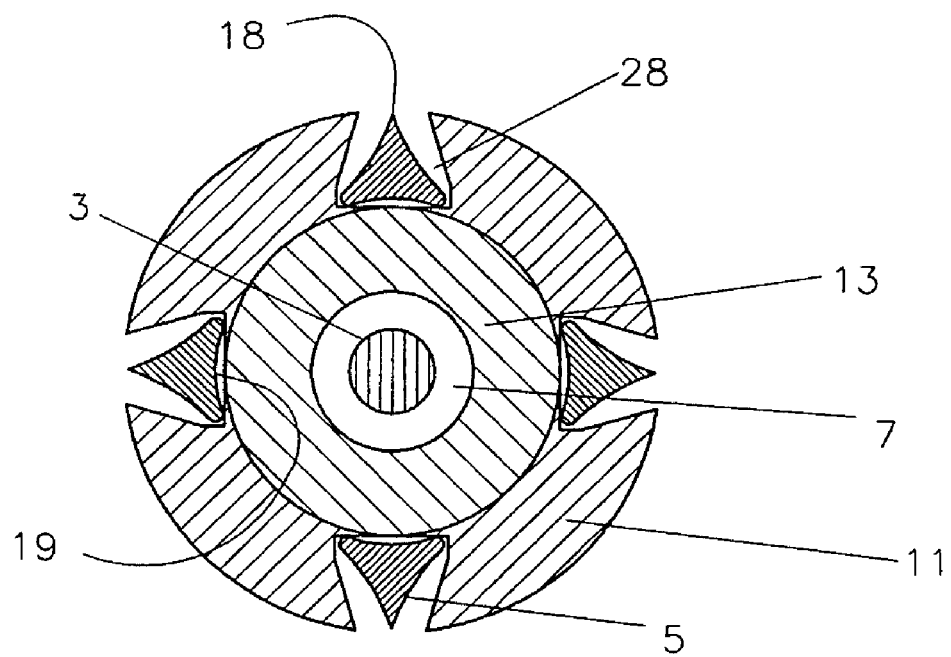
FIG. 2B is a cross-sectional view of the present device as seen along line 2B-2B in FIG. 1B.

FIG. 2B is a cross-sectional view of the device 1 of FIG. 1B along lines 2B-2B. The side openings 28 formed in tube 26 at the junction of tubular segments 11 and 12 provide a channel through which the cutting wire elements 5 are deployed or protracted from the tube 26 into the vessel. When fully retracted within the device 1 in an undeployed position, the cutting wire 5 ends are retained within the guide channels 14 and are disposed fully inside the exterior surface of the longitudinal housing below the level of openings 28 in the sidewall of the tube 26. The combined guide insert channels 14 and side hole openings 28 provide a passageway through which the wires 5 are deployed in vessel. This passageway also forms the channel through which the cutting wires 5 are retracted following completion of the procedure.

An alternative embodiment of the device 1 is shown in FIG. 3A and FIG. 3B. In this embodiment, the distal tubular jacket segment 11 and the proximal tubular jacket segment 12 are separate components with the guide insert 13 disposed between the two jacket members. The guide insert 13 connects the separate tubular jacket segments 11, 12 together. The guide insert 13 includes a recessed insert section 16 and a plurality of guide channels 14. In the embodiment shown, there are four radially equally spaced guide channels 14. The recessed insert sections 16 of guide insert 13 provide a lap joint connection between the distal and proximal tubular jacket segments 11 and 12. The recessed insert sections 16 have a smaller diameter than the exposed portion 17 of the insert guide 13. Exposed portion 17 of insert guide 13 is of the same outer diameter as the distal and proximal tubular jacket segments 11 and 12, providing a smooth outer profile along the entire length of the tube 26. The recessed insert sections 16 are in contact with the inner wall surface of tubular jacket segments 11 and 12. Preferably, the insert sections 16 are permanently bonded to the two tubular segments 11 and 12.

The conversion device 1 may optionally include an extension (not shown) of the distal tip area 10 to facilitate insertion and advancement of the device 1 through the catheter lumen and vasculature. The extension may be a spring-coiled guidewire-like tip approximately 1.5 cm in length. Other embodiments of the tip extension such as a flexible polymer tip may also be used. The extension provides a soft, atraumatic tip for improved tracking capabilities through the lesion. Alternatively, tubular jacket segments 11 and 12 may be made of different material. For example, the proximal tubular jacket segment 12 may be constructed of stiffer material such as polyamide and the distal tubular jacket segment may be constructed of softer, more flexible material such as an elastomeric polymer. In this configuration, the proximal end provides the stiffness and pushability required to advance the device. The softer, more-flexible distal segment provides for atraumatic navigation through torturous vasculature.

The conversion device 1 may also be constructed such that the tube 26 is integrally formed with angled deployment/retraction channels, eliminating the requirement for a separate insert guide component. In this embodiment, the wires are deployed through channels that are angled relative to the longitudinal axis of the tube. The acute angle of the channels relative to the axis of the shaft may range between 5 and 80 degrees.

Figure 4:
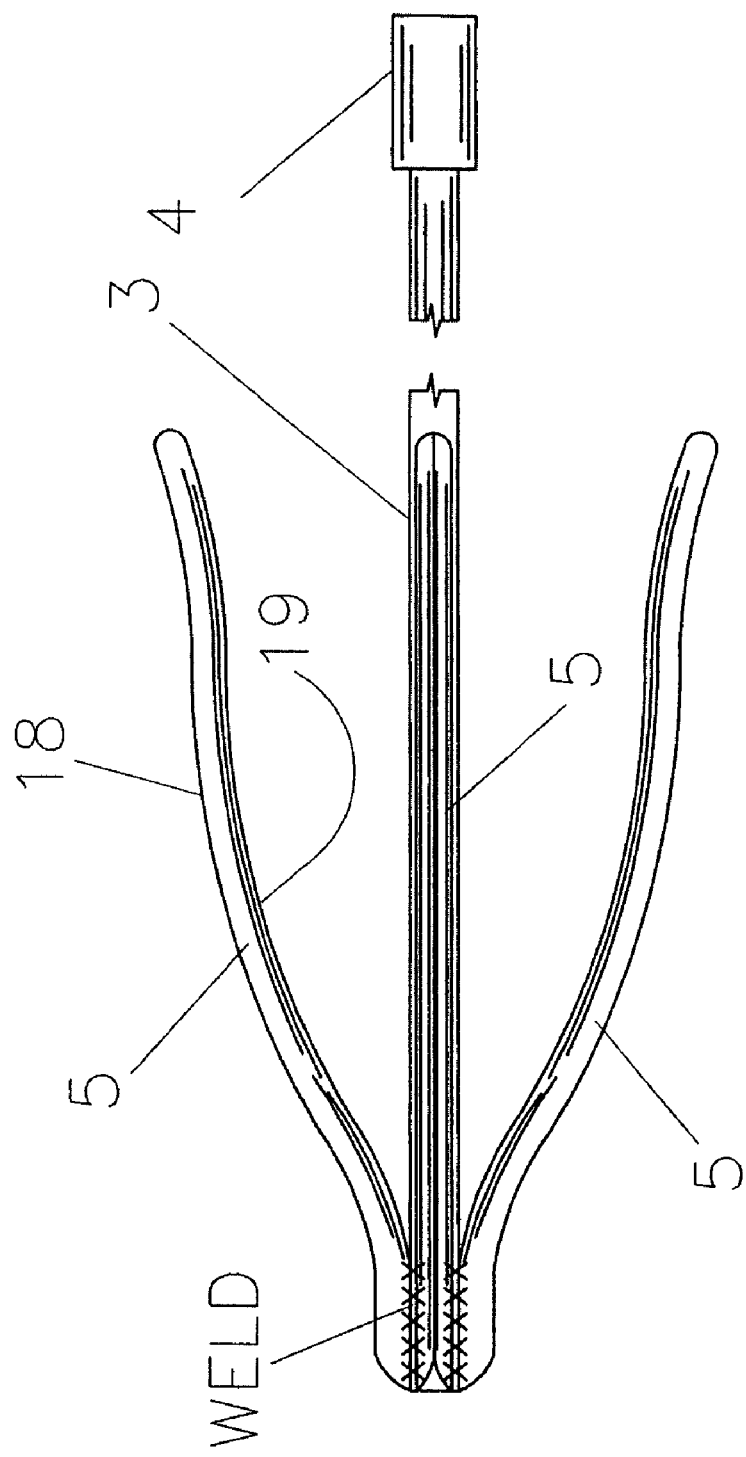
FIG. 4 is a plan view of the shaft and cutting wire components of the present invention in a deployed state.

FIG. 4 shows the shaft 3, handle 4 and cutting wire elements 5 in an unassembled state. The shaft 3 is attached to a plurality of cutting wire elements 5 at the distal end and a handle member 4 at the proximal end of shaft 3. One end of each cutting wire element 5, shown in a deployed configuration, is permanently attached to the distal portion of the shaft 3. Typically, the wire elements 5 are welded or bonded to the shaft 3. The shaft 3 is made of flexible medical grade stainless steel or other similar material such as shape memory metals. The cutting wire elements 5 are preferably made of shape-memory alloy such as nitinol as is well known in the art but other configurations are possible, including the use of a polymeric fiber material to form the cutting wire elements 5.

When positioned completely within the channel 7 of distal tubular jacket segment 11 as shown in FIG. 1A, the cutting wire elements 5 are in a stowed or undeployed position. At the proximal end, the wire elements 5 are confined between the channel 14 walls of the guide insert 13 and the side opening 28 walls of the distal tubular jacket segment 11, as depicted in both FIG. 2A and FIG. 2B. At the distal end the wire elements 5 are within the channel 7, enclosed by the inner wall of tubular distal jacket member 11. In the embodiment shown in FIG. 3A, the free ends of the cutting wire elements 5 are confined between the shaft 3 and the inner walls of channel 14 of the guide insert 13. Thus, when in the retracted or stowed position, the wire elements 5 are enclosed within the device 1 and accordingly are not exposed to the vessel wall to avoid accidental cutting of the vessel wall.

The handle member 4 of shaft 3 provides a positioning function of the shaft 3 relative to the distal tubular jacket 11. When the handle member 4 is in contact with the proximal end of the tubular segment 12 as shown in FIG. 3A, the device 1 is in a fully retracted undeployed position. When the proximal tubular jacket segment 12 is advanced, forward and away from the handle 4, the tube 26 moves away from the handle, and as illustrated in FIG. 1B, the cutting wires 5 are deployed. The wires 5 are fully deployed when the tubular jacket segment 12 cannot be advanced further. Advancement of tubular jacket segment 12 is stopped by a physical stop when the guide insert 13 contacts the weld area where the shaft 3 and wire elements 5 are joined.

The shape-memory characteristic of the alloy pre-dispose the cutting wire elements 5 to conform to the expanded umbrella shape shown in FIG. 4 when deployed into the vessel. When deployed, the wires 5 expand into an umbrella-like configuration with the cutting edges 18 facing outward against the vessel wall.

Figure 5:
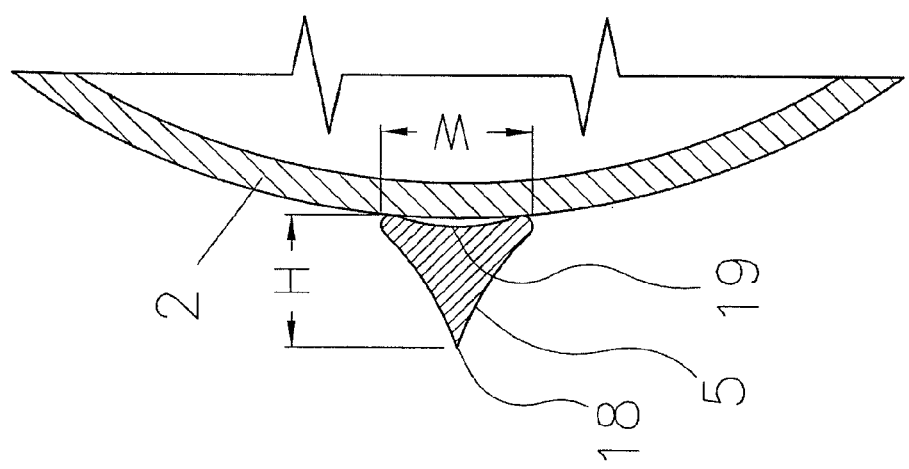
FIG. 5 is partial cross-sectional view of an inflated angioplasty balloon with the cutting wire element of the present invention.

FIG. 5 depicts a partial cross-sectional view of a balloon 2 of a standard balloon catheter 24 (FIG. 12) in an inflated state with the cutting wire 5 in the deployed position. Each cutting wire element 5 has a triangular cross-section with a single cutting edge 18 and a curved base 19 having a concave shape with respect to the balloon 2. When the balloon 2 is inflated, the cutting edges 18 come in contact with the stenotic vessel wall, causing longitudinal incisions along the lesion 22 (see FIG. 12). The curved base 19 provides an alignment function of the cutting wires 5 relative to the outer balloon surface when the balloon 2 is inflated and the cutting wires 5 are deployed. The curved base 19 of each cutting wire 5 rests against and follows the curvature of the outer balloon surface. Specifically, the curved base 19 rests against the inflated balloon surface, ensuring that the cutting edge 18 is perpendicular to the balloon surface to face the lesion surface. The edges of the curved base 19 are radiused to provide a smooth contact area between the balloon 2 surface and the cutting wire elements 5 and to prevent unintended damage to the balloon 2.

In the embodiment shown, each wire 5 consists of a single integrated longitudinal blade having a continuous longitudinal edge 18. Other wire configurations are possible, however. For example, the wire 5 may simply consist of a guidewire or any other wire having no sharp edges. Alternatively, instead of a continuous longitudinal edge 18, the wire 5 may have segments of edges that are spaced from each other for making a series of smaller incisions. In another alternative, the wire 5 may consist of one or more smaller blades that are mounted on a common base. Each blade can be positioned longitudinally or transversely with respect to the common base.

The dimensions of cutting wire element 5 with a wider base width W than wire height H (W:H$>=$1) ensures that the wires are deployed with the cutting edge 18 pointing toward the lesion surface. In one embodiment, the height of the cutting segment 18 of the wire 5 is between 0.005" and 0.012" with a curved base 19 being greater than 0.012". In addition to the dimensions, the shape-memory characteristics of the wire elements 5 will ensure that the wires are deployed with the cutting edges 18 positioned away from the balloon surface and facing the lesion. Although four cutting wires 5 are depicted in the embodiment as shown in FIGS. 2A and 2B, a single cutting wire or a plurality of cutting wires other than four wires are also possible.

Although the base 19 has a concave shape in the embodiment shown, the base may be straight rather than radiused. So long as the base 19 of the cutting wire element 5 rests against the balloon surface, the device performs as intended. Other wire configurations are also possible including a standard guidewire profile with no cutting edges. Any wire configuration that functions to provide sufficient focused pressure against the lesion to generate a fracture can be used with the present invention.

A method of using the present invention to convert a standard balloon catheter into a cutting balloon catheter will now be described with reference to FIG. 6 through FIG. 14. Although the method describe herein is for a standard angioplasty procedure, the device and method of this invention can be used to treat medical conditions for both vascular and non-vascular applications including dialysis grafts, native fistulas, biliary or other ductal structures, peripheral and coronary stenoses, and peripheral and coronary restenosis associated with prior angioplasty or stent placement.

Figure 6:
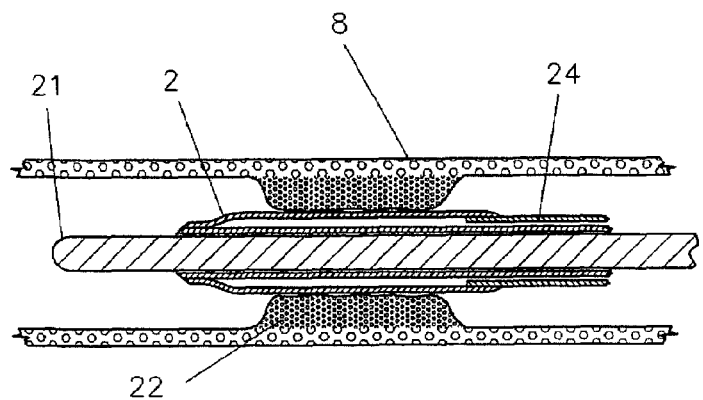
FIG. 6 is a sectional view of an un-inflated angioplasty balloon catheter with guidewire within a stenotic vessel.

In preparation for an angioplasty procedure, a guidewire 21 is first inserted and advanced to the target lesion 22 using fluoroscopic visualization. An angioplasty balloon catheter 24 is then inserted into the vessel 8 over the guidewire 21 and advanced until the balloon 2 is positioned across the stenotic lesion 22 as shown in FIG. 6. The angioplasty balloon 2 is slowly inflated causing the balloon 2 to expand and move outwardly in a radial direction to contact the stenotic wall. Further dilation of the balloon 2 is then performed in an attempt to sufficiently open the lesion 22 and dilate the lumen of the vessel 8.

If the balloon 2 fails to dilate the vessel 8 sufficiently, conventionally the standard catheter 24 had to be removed and exchanged with a cutting balloon catheter. Moreover, the catheter exchange may require an exchange of the guidewire as well. According to the present invention, however, the conversion device 1 is used to convert the existing standard balloon catheter 24 already in position in the vessel 8 into a cutting balloon catheter.

Figure 7:
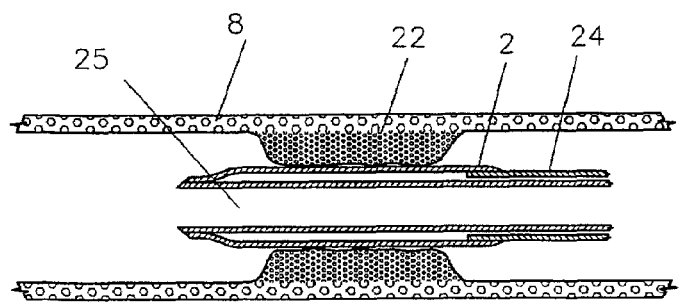
FIG. 7 is a sectional view of an un-inflated angioplasty balloon catheter without guidewire within a stenotic vessel.
Figure 8:
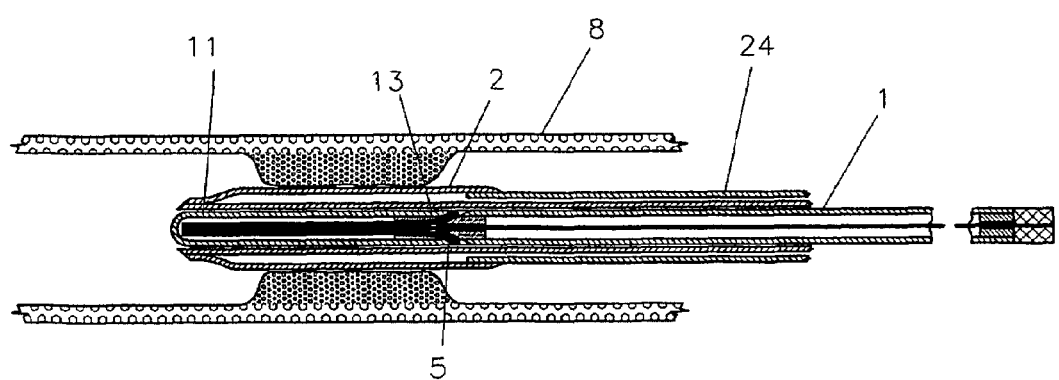
FIG. 8 is a sectional view of the present device within the lumen of the angioplasty balloon catheter of FIG. 7 prior to deployment.

According to the inventive method, the guidewire 21 is removed as shown in FIG. 7. The balloon 2 is then deflated but not removed from the vessel 8. Instead, the conversion device 1 is inserted into the guidewire lumen 25 of the angioplasty catheter 24 and advanced until the distal tubular jacket segment 11 and guide insert section 13 are within the balloon segment of the angioplasty catheter 24. The position of the conversion device 1 relative to the angioplasty balloon is shown in FIG. 8.

Because the conversion device 1 is inserted, advanced and deployed from within the lumen 25 of the angioplasty catheter 24, the problems encountered with prior art cutting balloon technology are eliminated. Specifically, larger overall device profiles due to cutting blades placed externally on the balloon as well as difficulties of advancing through tortuous vasculature due to the larger size and stiffness are eliminated with the present invention.

In preparation for the deployment of the cutting wires 5, the angioplasty balloon catheter 24 is withdrawn from the lesion 22 to a point just proximal to the lesion 22 while the conversion device 1 is held stationary. Re-positioning the balloon catheter 24 just proximal to the lesion allows for clear deployment of the wires within the vessel. As is well known in the art, radiopaque markers on the balloon catheter 24 and the conversion device 1 can be used to indicate correct positioning of the balloon relative to the distal portion of the conversion device 1 prior to deployment.

Figure 9:
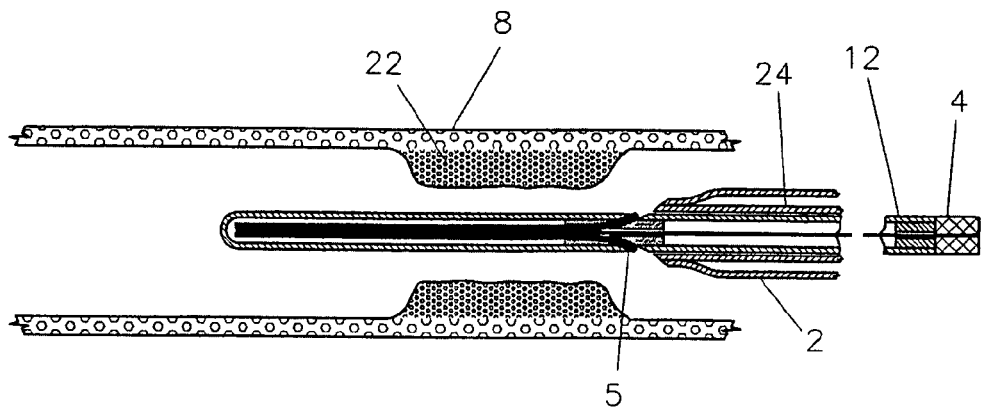
FIG. 9 is a sectional view of the present device within the lumen of the angioplasty balloon catheter after retraction of balloon catheter of FIG. 7 and prior to deployment.

Balloon position relative to the stenotic lesion 22 and the conversion device 1 prior to wire deployment is depicted in FIG. 9. As illustrated, there is no need with the present invention to exchange the angioplasty balloon catheter 24 with a different cutting balloon device. Instead, the balloon 2 is temporarily repositioned just proximal of the lesion 22 to allow for clear deployment of the wires 5 and then returned to the original position within the lesion 22 in preparation for angioplasty.

Figure 10:
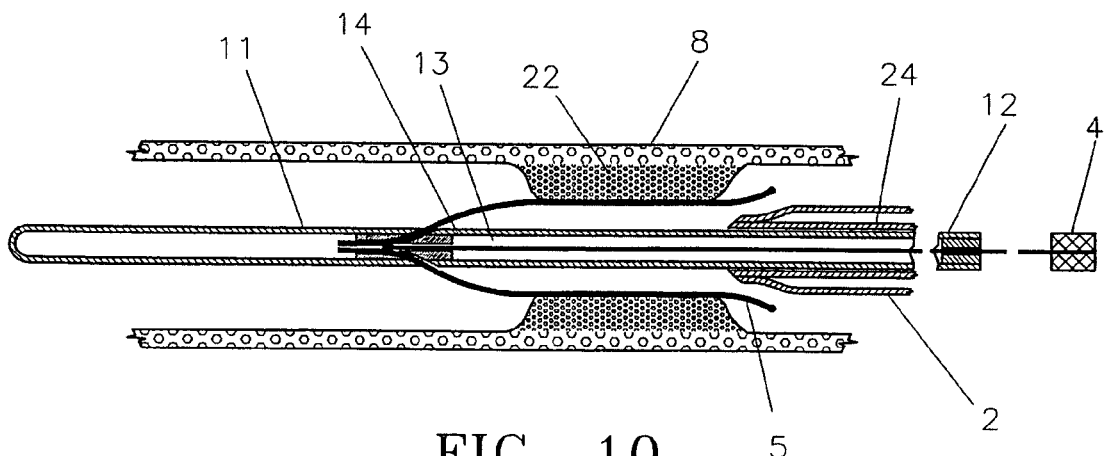
FIG. 10 is a sectional view of the present device after deployment within the vessel.

To deploy the cutting wires 5, the handle member 4 is held stationary while the user advances the outer tubular jacket member 12. Advancing the outer tubular member 12 causes the guide insert 13 and the distal tubular member 11 to also advance. This action results in the deployment of the cutting wires 5, as illustrated in FIG. 10. Specifically, as the outer tubular member 11 and insert 13 are moved distally past the stenotic lesion 22, the cutting wires 5 extend out from the tube 26 through the guide channels 14, through the openings 28 on the sidewall of the tube 26 and into the vessel 8. The shape-memory characteristics of the cutting wires 5 cause them to expand radially outward in an umbrella formation to contact the stenotic lesion 22 of the vessel 8 wall.

When being deployed this way, the cutting wires 5 extend outside of the outer tubular member 11 without longitudinally moving. Instead, the outer tubular member 11 moves. This is important because it ensures that the free ends of the cutting wires 5 do not penetrate or snag on the inner wall of the vessel 8 or the lesion 22, which may prevent full deployment of the wires.

The design of the present invention allows for the user to adjust the length of extended cutting wire elements 5 to accommodate various length balloons. By controlling the amount of advancement of the tubular member 12, the user can select the length of exposed wire elements 5. This feature allows the use of a single device 1 with any length PTCA (percutaneous transluminal coronary angioplasty) or PTA (percutaneous transluminal angioplasty) balloon. Similarly, use of the device 1 is not restricted to a specific diameter balloon configuration, as the standard cutting balloons require. The umbrella configuration of the deployed cutting wires conforms to various size diameter angioplasty balloons. Accordingly, the inventory requirements of an angioplasty suite are greatly reduced.

As discussed in the background section, a typical cutting balloon currently on the market has a maximum inflation pressure of only 8 atms while that of a standard high pressure angioplasty balloon can go up to 30 atms or more. Since the present device 1 can be used with a standard high pressure angioplasty balloon to convert the same into a cutting balloon, the inflation pressure of the converted balloon with the deployed cutting wires 5 may be increased substantially past the maximum 8 atm of a conventional cutting balloon, if needed. Alternatively, because of the higher maximum pressure, the edge 18 of the cutting wires 5 may be less sharp than the edge of a standard cutting balloon catheter.

Figure 11:
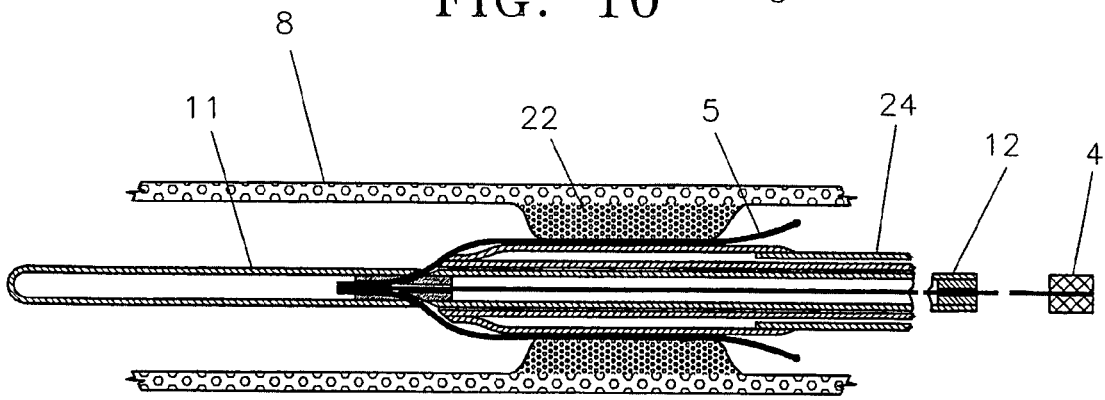
FIG. 11 is a sectional view of the present device after the angioplasty balloon has been repositioned within the stenosis.

Once the cutting wires 5 are deployed, the angioplasty catheter 24 is re-advanced into the target lesion 22 and positioned within and under the umbrella formation as shown in FIG. 11. The balloon 2 is still deflated at this point. After confirming position of the balloon 2 relative to the lesion 22 and cutting wires 5, the device is re-inflated. This action causes the balloon 2 to expand and contact the cutting wires 5. Further inflation results in force being applied by the balloon 2 surface to the cutting wires 5 which in turn causes focal concentrated force to be applied by the cutting edges 18 of the wire 5 to the stenotic mass. The cutting edges 18 score the lesion creating incision lines in the lesion 22. In the context of the present invention, scoring is defined as a focalized fracture or cutting of the lesion 22. As such, scoring of the lesion 22 may be achieved by using either a wire having a dull edge or a sharp edge.

Figure 12:
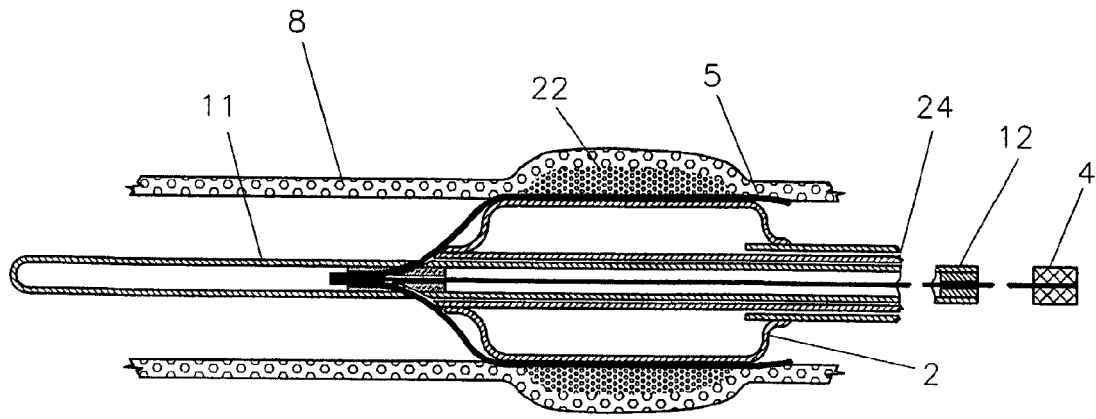
FIG. 12 is a sectional view of the present device after the angioplasty balloon has been inflated.

Additional balloon pressure causes the incision lines to propagate, easing the expansion of the vessel 8 as shown in FIG. 12. Because the cutting wire edges 18 produce such high focal stress along the lesion surface, significantly less balloon pressure than traditional angioplasty is required to open the vessel.

Figure 13:
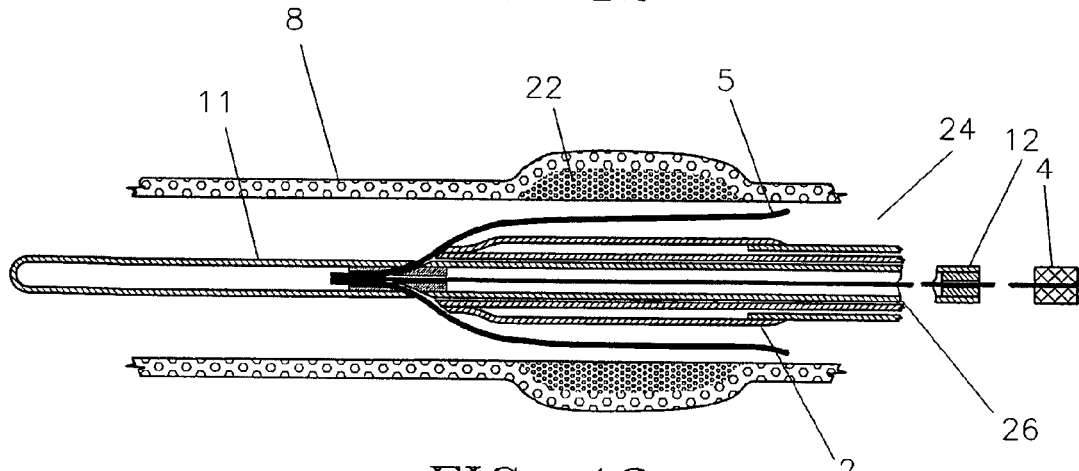
FIG. 13 is a sectional view of the present device after the angioplasty balloon has been deflated.
Figure 14:
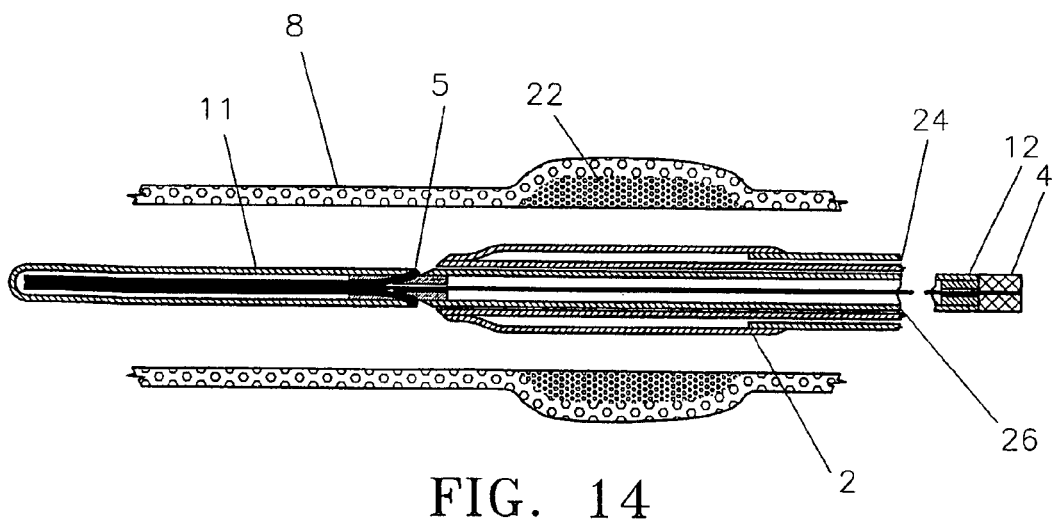
FIG. 14 is a sectional view of the present device after the wire elements of the device have been retracted.

Once the vessel 8 lumen is sufficiently dilated, the balloon 2 is deflated, as shown in FIG. 13. The cutting wires 5 are then retracted within the distal segment 11 of the tube 26. To retract the cutting wires 5, the handle member 4 is pushed distally while the tubular jacket member 12 is held stationary. This action causes the cutting wires 5 to advance forward through the channels 28 of the tube 26, through the channels 14 of the guide insert and into the stowed and undeployed position within the channel 7 of the distal tubular jacket segment 11. Retraction is complete when the entire length of cutting wires 5 are fully enclosed within the tube 26 as shown previously in FIG. 14.

Alternatively, the cutting wires 5 may be retracted within the distal segment 11 of the tube by first withdrawing the deflated balloon proximally from the lesion. The handle member 4 is held stationary while the proximal tubing segment 12 is pulled proximally toward the handle. This action causes the distal tubing segment 11 to move proximally and results in the wires being drawn into the side channels 28.

An alternate method of deployment may be used in certain situations such as when the lumen of the lesion 22 is sufficiently tight or small that the wires 5 may not deploy properly or that the deployed wires may not provide sufficient space for the balloon. In those situations, instead of positioning the distal portion 11 directly within the lesion 22, it can be positioned just proximally of the lesion and deployed. Once the balloon of the catheter 5 is positioned under the deployed cutting wires, the deployed wires and the un-inflated catheter 24 can be pushed together for positioning within the lesion 22 as shown in FIG. 11.

The present device 1 can be lengthened to accommodate the exchange of balloon catheters or other dilation devices. For example, if an originally placed balloon catheter needs to be exchanged because it is not working properly or is of insufficient diameter or length to adequately cover the target lesion area, the catheter can be removed while leaving the conversion device 1 in place within the vessel 8. The replacement catheter can then be back loaded over the proximal end of the housing 26 and advanced to the lesion area. The only device modification required to maintain access during catheter exchanges would be to increase the length of the housing 26 to ensure that the length of the housing 26 outside of the patient is longer than the entire length of the catheter being exchanged. Thus the device 1 acts as a guidewire, eliminating the need for multiple exchanges of guidewires, as well as a cutting or scoring instrument.

As can be appreciated by persons of skill in the art, problems associated with withdrawal of conventional cutting balloons are eliminated with the design of the present invention. Since the cutting wires are completely contained and enclosed within the tubular jacket segment 11 after retraction, there is no chance of inadvertent vessel wall damage by cutting elements during withdrawal of the device.

Once the cutting elements are retracted, the conversion device 1 can then be withdrawn from the vessel. Once removed, a guidewire is re-inserted through the lumen 25 of the balloon catheter 24 to maintain access to the vessel, if desired. The balloon catheter 24 is then removed from the vessel. To complete the procedure, an angiogram is typically performed to determine vessel patency. Once the angiogram has confirmed acceptable results, the guidewire is then removed from the vasculature.

FIG. 15A and FIG. 15B illustrate an alternative embodiment which may be useful in certain situations where plaque cutting in tortuous, curved vasculature such as arterial-venous fistulas and dialysis grafts is needed. In this embodiment, the wire elements 5, shaft 3 and distal tubular jacket 11 are all in a pre-curved or bent configuration in the same direction as shown in FIG. 15A which illustrates the device 1 prior to insertion into the lumen of the catheter 24 or after the device is withdrawn from the catheter. FIG. 15B illustrates the device 1 in a deployed state as if it's positioned within the vessel 8 where the distal portion 11 tends to straighten out to follow the contour of the vessel. When the conversion device 1 is inserted into and advanced through the balloon catheter lumen, the pre-set curve profile will straighten and conform to the lumen of the catheter 24 due to the relatively flexible nature of the housing and the wires 5, particularly the distal segment 11. The cutting wire elements 5 are then deployed using the methods as previously described. The pre-set curve profile of the distal end of device 1 and of the cutting wire elements 5 prevents the wire elements from deploying in a non-symmetrical configuration. A straight device deployed in a curved section of the body lumen may cause non-uniform radial spacing of the wires 5 relative to the axis of the vessel. In addition, the wires 5 may twist and not be optimally aligned with the vessel's axis when fully deployed. In contrast, the pre-set curve profile of the device 1 depicted in FIG. 15A and FIG. 15B will tend to align with the curvature of the catheter, which follows the contour of the vessel. Thus, in this embodiment, the wires 5 are deployed in a relatively symmetrical manner against the inner vessel wall.

According to the invention, balloon deflation and withdrawal problems, which are common during angioplasty procedures, will not be complicated by external blade structures found on prior art cutting balloons. With the present invention, the cutting wires 5 are completely contained within the conversion device 1, which is designed to be withdrawn independently of the balloon catheter.

While certain novel features of this invention have been shown and described above, the present invention may be embodied in other specific forms without departing from the spirit or essential characteristics of the invention such as different delivery mechanism, materials, configurations and different cutting wire designs. The described embodiments are to be considered in all respects only as illustrative and not as restrictive.

Clearly, the invention also envisions different cutting wire deployment mechanisms and wire configurations. Deployment can be achieved by numerous methods including the use of a shape-memory material, by longitudinal movement of the wires through a channel, by radial expansion using a mechanical release mechanism or by a combination of any of the above deployment methods. For example, a deployment mechanism may be designed so that the undeployed wires are deployed by having free ends of the wires extend radially away from the longitudinal housing similar to the way an umbrella opens, instead of the wires sliding out of the sidewall openings of the longitudinal housing. A mechanism lever or release mechanism may be used to control deployment and/or retraction of the wires relative to the device.

The housing design can also be modified to include a guide having one or more U-shaped channels to deploy a single or multiple wires. The U-shaped channels guide the wires to be deployed in the proximal direction which is generally parallel to the longitudinal axis of the housing 26 by advancing the shaft distally. This design may be advantageous in certain situations because it minimizes the length of the distal portion 11. If a single cutting wire 5 is used, then the wire may be simply an extension of the shaft 3.

Various omissions, modifications, substitutions and changes in the forms and details of the device illustrated and in its operation can be made by those skilled in the art without departing in any way from the spirit of the present invention.

What is claimed is:

1. A method of treating a lesion in a body lumen comprising the steps of:

inserting, through a lumen of an intraluminal device having an expandable member, a longitudinal housing having at least one cutting wire in an undeployed position entirely within the housing, after said step of inserting, extending the wire outside of the longitudinal housing in a proximal direction and substantially longitudinally positioning the wire between the lesion and the expandable member of the intraluminal device to provide a deployed state of said wire, and after said step of extending and positioning the wire, expanding the expandable member to force the wire against the lesion.

2. The method of claim 1 wherein said step of extending said wire includes the step of: distally moving the longitudinal housing with respect to the wire causing one end of the wire to extend proximally out through an opening in the side wall of the longitudinal housing.

3. The method of claim 1 further comprising the step of: proximally moving the longitudinal housing with respect to the deployed wire to retract the deployed wire through an opening in the side wall of the housing to a position entirely within said longitudinal housing.

4. The method of claim 1 wherein: said cutting wire has a longitudinal edge.

5. A method of treating a lesion in a body lumen comprising the steps of:

inserting, through a lumen of a balloon catheter, a longitudinal housing having a cutting wire in an undeployed position entirely within the housing after said step of inserting, extending the wire outside of the longitudinal housing in a proximal direction and substantially longitudinally positioning the wire between the lesion and the balloon of the balloon catheter to provide a deployed state of said wire, and after said step of extending and positioning the wire, inflating the balloon of the catheter to force the wire against the lesion.

6. The method of claim 5 wherein: said step of extending the wire includes the step of: distally moving the longitudinal housing with respect to the wire causing one end of the wire to extend proximally out through an opening in the side wall of the longitudinal housing.

7. The method of claim 6 further comprising the step of: proximally moving the longitudinal housing with respect to the deployed wire to retract the deployed wire through an opening in the side wall of the housing to a position entirely within said longitudinal housing.

8. The method of claim 7 further comprising the steps of: deflating the balloon and longitudinally moving the balloon catheter away from the wire prior to said step of proximally moving said longitudinal housing.

9. The method of claim 5 further comprising the step of: positioning said balloon of said balloon catheter under the extended wire after said step of extending said wire and before said step of inflating said balloon.

10. The method of claim 5 wherein: said cutting wire has a longitudinal edge.

11. A method of treatment of a lesion in a body lumen, comprising the steps of:

providing a longitudinal housing having cutting wires deployable between a retracted state entirely within the longitudinal housing and a protracted state extending substantially longitudinally outside the longitudinal housing;

inserting the longitudinal housing having cutting wires through a lumen of an intralumenal device having an inflatable balloon;

positioning the longitudinal housing within the body lumen with the wires in a retracted state entirely within the housing, protracting the wires by extending the wires in a proximal direction into a substantially longitudinal protracted state, adjacent to a lesion in a body lumen;

when the wires are in their protracted state, moving an inflatable balloon in a deflated state between the wires and the longitudinal housing;

inflating the balloon to force the wire against the adjacent lesion;

deflating the balloon, and retracting the wires into their retracted state.

* * * * *